United States Patent

DeJacma

[11] Patent Number: 6,080,165
[45] Date of Patent: Jun. 27, 2000

[54] SELF-CONTAINED DISPOSABLE HANDPIECE FOR A SKIN TISSUE REMOVING APPARATUS

[76] Inventor: Frederick W. DeJacma, P.O. Box 9787, Arnold, Md. 21012

[21] Appl. No.: 09/267,664

[22] Filed: Mar. 15, 1999

[51] Int. Cl.$^7$ ........................................ A61B 17/50
[52] U.S. Cl. .............................................. 606/131
[58] Field of Search ..................... 606/131, 132, 606/159; 604/289, 290, 313, 315

[56] References Cited

U.S. PATENT DOCUMENTS

| | | |
|---|---|---|
| 5,037,432 | 8/1991 | Molinari . |
| 5,100,412 | 3/1992 | Rosso . |
| 5,810,842 | 9/1998 | Di Fiore et al. . |
| 5,971,999 | 10/1999 | Naldoni ................................... 606/131 |

*Primary Examiner*—Paul J. Hirsch
*Assistant Examiner*—Michael B. Priddy
*Attorney, Agent, or Firm*—Venable; Gabor J. Kelemen

[57] ABSTRACT

A manually held and guided handpiece for a skin tissue removing apparatus includes a mixing container accommodating unused abrasive crystals and having a front end and an air inlet opening spaced from the front end. A delivery tube extends within the mixing container and has opposite first and second open ends. The first open end is situated at the front end of the mixing container and the second open end is situated at a distance from the air inlet opening. A collecting container accommodates particles composed of used abrasive crystals and dislodged skin tissue fragments. The collecting container has a front end and an air outlet opening spaced from the front end of the collecting container and being connectable to a vacuum source. An exit tube extends within the collecting container and has opposite first and second open ends. The first open end of the exit tube is situated at the front end of the collecting container and the second open end of the exit tube is situated at a distance from the air outlet opening. A connecting channel couples the first open end of the delivery tube with the first open end of the exit tube. A treatment window in the connecting channel is adapted to be brought into contact with the surface of a patient's skin. An air stream maintained through the handpiece carries the crystals which impinge on the skin before re-entering the treatment window and are deposited in the collecting container, together with skin fragments.

10 Claims, 1 Drawing Sheet

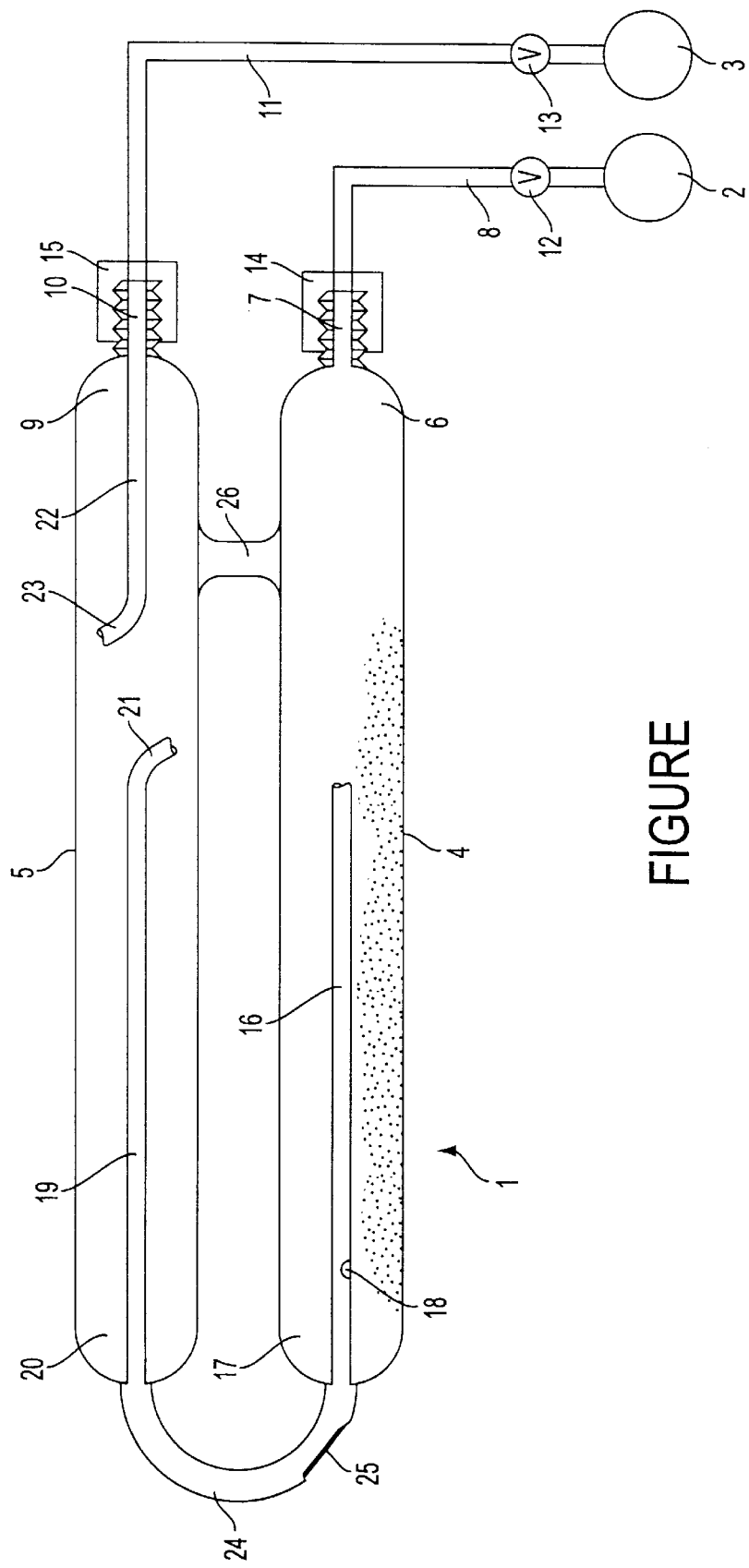
FIGURE

SELF-CONTAINED DISPOSABLE HANDPIECE FOR A SKIN TISSUE REMOVING APPARATUS

FIELD OF THE INVENTION

This invention relates to an apparatus for removing human skin tissue (microdermoabrasion) by a stream of abrasive crystals and is more particularly concerned with a handpiece for applying the abrasive crystal stream to and removing the crystals and dislodged skin tissue fragments from the human skin.

BACKGROUND OF THE INVENTION

Tissue removal by directing an air stream carrying an abrading agent (such as corundum crystals) onto human skin has been known, as disclosed, for example, in U.S. Pat. Nos. 5,037,432, 5,100,412 and 5,810,842.

Surface skin tissue removal may be indicated for various skin conditions, such as scars, wrinkles, abnormal pigmentation, stretch marks, tattoos, burns, etc.

It is a common characteristic of the prior art constructions to supply the abrasive-laden air stream to the handpiece by a flexible pressure line leading from a mixing bulb which has a capacity of, for example, one or two pints. Compressed air is introduced into the mixing bulb which accommodates the abrasive crystals (having a grain size of, for example, 120 micron). The air stream carries the abrasive crystal from the mixing bulb through the pressure line to the handpiece, and the operator manually guides the handpiece in gentle contact with the skin surface, whereby the skin is being bombarded by the abrasive crystals as they exit through a handpiece opening facing and being generally obturated by, the skin surface.

After impinging on the skin, the abrasive crystals, entrained by a low-pressure (vacuum) air flow, immediately re-enter the handpiece together with the dislodged skin particles and exit from the handpiece through a vacuum leading into a collecting bulb which also may be of a one-pint capacity, and which may be situated adjacent the mixing bulb. The collecting bulb is coupled to a vacuum source so that a continuous closed flow is maintained to continuously pelt the skin surface with fresh abrasive crystals from the mixing bulb supplied by the pressure flow and then immediately withdraw the used crystals and dislodged skin fragments in the vacuum flow.

Like for any medical instrument, sterilization of the handpiece and the collecting bulb before reuse has been a principal consideration. Also, strict measures have to be taken to maintain both the mixing bulb and the collecting bulb well isolated from the environment. These requirements involve stringent and involved measures, particularly when the apparatus is used in the field.

SUMMARY OF THE INVENTION

It is an object of the invention to provide an improved handpiece for a human skin treating apparatus of the above-outlined type which renders the treating apparatus more compact and which is disposable, thereby preventing contamination of patients and medical personnel in a simpler and safer manner.

This object and others to become apparent as the specification progresses, are accomplished by the invention, according to which, briefly stated, the manually held and guided handpiece for a skin tissue removing apparatus includes a mixing container accommodating unused abrasive crystals and having a front end and an air inlet opening spaced from the front end. A delivery tube extends within the mixing container and has opposite first and second open ends. The first open end is situated at the front end of the mixing container and the second open end is situated at a distance from the air inlet opening. A collecting container accommodates solid particles composed of used abrasive crystals and dislodged skin tissue fragments. The collecting container has a front end and an air outlet opening spaced from the front end of the collecting container and being connectable to a vacuum source. An exit tube extends within the collecting container and has opposite first and second open ends. The first open end of the exit tube is situated at the front end of the collecting container and the second open end of the exit tube is situated at a distance from the air outlet opening. A connecting channel couples the first open end of the delivery tube with the first open end of the exit tube. A treatment window is provided in the connecting channel and is adapted to be brought into contact with the surface of a patient's skin. A stream of air forced to enter in the air inlet opening of the mixing container and exit the outlet opening of the collecting container entrains unused abrasive crystals from the mixing container through the delivery tube and causes the abrasive crystals to pass through the treatment window, to impinge upon the skin surface, to re-enter the treatment window with dislodged skin tissue fragments and to be deposited, with the skin fragments in the collecting container.

BRIEF DESCRIPTION OF THE DRAWING

The sole FIGURE is a side elevational view of a preferred embodiment of the invention.

DESCRIPTION OF THE PREFERRED EMBODIMENT

Turning to the FIGURE, the apparatus for removing surface tissue of the human skin shown therein essentially includes a handpiece generally designated at 1 and structured according to the invention, as well as a pressure source 2 and a vacuum source 3 (both only symbolically shown) coupled to the handpiece 1.

The body of the handpiece 1 is composed essentially of two parallel-spaced, rigidly interconnected, generally cylindrical, hollow components, namely, a mixing bulb (mixing container) 4 and a collecting bulb (collecting container) 5. Typically, the handpiece 1 is of a clear, transparent, rugged material, such as glass, Plexiglas or similar plastic material. The handpiece 1 is dimensioned such that it may be comfortably held by the operator like a large pencil. It has an overall length of, for example, approximately 7 inches and an overall height of about 2 inches. Each bulb 4 and 5 may have a diameter of approximately 0.75 inch.

The mixing bulb 4 has an externally threaded rear terminus 6 defining an air inlet opening 7 which is in communication with the pressure source 2 by means of a flexible pressure line 8. The collecting bulb 5 has, adjacent the terminus 6 of the mixing bulb 4, a rear terminus 9 defining an air outlet opening 10 which is in communication with the vacuum source 3 by means of a flexible vacuum line 11. The pressure line 8 and the vacuum line 11 contain respective flow control valves 12 and 13 which may be individually controlled either manually, for example, by rotating a control knob or by means of a foot pedal. The lines 8 and 11 are readily removably and sealingly attached to the respective bulbs 4 and 5 by screw caps 14 and 15 screwed on the respective threaded rear terminus 6 and 9.

A rigid delivery tube 16, open at both ends, is sealed to the front end 17 of the mixing bulb 4. The tube 16 extends generally axially within the mixing bulb 4 and terminates beyond the longitudinal middle thereof. The mixing bulb 4 contains unused abrasive crystals, such as 120 micron size corundum crystals which may be placed into the mixing bulb 4 during manufacture and are sealed thereinto, for example, by providing a removable seal which covers the air inlet opening 7 and which is peeled off just before use. The tube 16 is provided with a crystal intake hole 18 located approximately 1 inch from the front end 17 of the mixing bulb 4. Expediently, before use, the fill level of the abrasive crystals is approximately ⅛ inch below the free end of the delivery tube 16 viewed when the handpiece 1 is in an upright position, with the front end 17 of the mixing bulb 4 pointing downward.

A rigid exit tube 19, open at both ends, is sealed to the front end 20 of the collecting bulb 5. The exit tube 19 extends generally axially within the collecting tube 5 and terminates, beyond its longitudinal middle, in a short bent tube portion 21. A further exit tube 22 open at both ends and having a short initial tube portion 23 bent in a direction away from the short tube portion 21 of the exit tube 19, extends to the rear terminus 9 of the collecting bulb 5 and is sealed thereto. The exit tube 22 is thus in direct communication with the air outlet opening 10 of the collecting bulb 5.

The open end of the delivery tube 16 at the front end 17 of the mixing bulb 4 and the open end of exit tube 19 at the front end 20 of the collecting bulb 5 are coupled to one another by a curved connecting tube (connecting channel) 24 which is provided with an aperture (treatment window) 25 in alignment with the delivery tube 16. In use, the treatment window 25 is brought into contact with the human skin and is, during such contacting, guided over the skin as the operator moves the handpiece 1. To ensure a smooth contacting of the curved connecting tube 24 with the human skin in the region of the treatment window 25, the bordering edges of the latter are suitably rounded.

For reinforcing the holding effect of the connecting tube 24 which positions and immobilizes the mixing bulb 4 and the collecting bulb 5 with respect to one another, in the vicinity of their rear terminus 6 and 9, the two bulbs 4 and 5 are interconnected by a web 26 formed on the exterior of the bulbs 4 and 5.

To prepare for treatment, an unused handpiece 1, whose mixing bulb 4 accommodates the sealed-in abrasive crystals, is coupled to the pressure line 8 and the vacuum line 11 after removing any peel-off sealing tapes or other temporary plugs from the handpiece 1.

By opening the flow control valve 13, air is drawn from the collecting bulb 5 through the vacuum line 11. Before bringing the treatment window 25 in contact with the skin, that is, before the skin surface blocks the treatment window 25, air is drawn therethrough and through the exit tubes 19 and 22, whereby a vacuum flow is maintained. During this operational phase, that is, before the treatment window 25 contacts the skin surface, the vacuum flow produces no flow through the mixing bulb 4, since air is drawn into the system solely through the open treatment window 25.

Treatment is started as the handpiece 1 is brought into contact with the patient's skin such that the skin surface substantially obturates the treatment window 25. Such a blocking of the window 25 thus forces air to be drawn from the mixing bulb 4 through the delivery tube 16 to maintain the air flow into the vacuum source 3.

The air flow through the delivery tube 16 draws abrasive crystals through the free tube end, as well as through the hole 18 into the delivery tube 16. The entrance hole 18 in the wall of the delivery tube 16 thus constitutes a second crystal inlet into the delivery tube 16 and contributes to a balanced intake flow of the abrasive crystals into the delivery tube 16. This is of particular significance in case the unused crystal quantities in the mixing bulb 4 have been reduced, so that the crystal intake rate through the free tube end has appreciably dropped.

The crystal-laden air stream travels through the delivery tube 16 into the connecting tube 24 and the crystals, continuing their linear travel, pass through the treatment window 25 and impinge on the skin area facing and obturating the window 25. The vacuum flow maintained in the connecting tube 24 draws the used crystals, together with dislodged skin tissue fragments through the treatment window 25 into the connecting tube 24. The particle-laden air flows through the exit tube 19 and is introduced through the short bent tube portion 21 into the collecting bulb 5 where the used abrasive crystals and the dislodged skin fragments are deposited. The air stream, stripped of the solid substances, enters the short bent initial tube portion 23 and the exit tube 22 and is drawn through the air outlet opening 10 of the collecting bulb 5 and the vacuum line 11 into the vacuum source 3. The opposite orientation of the bent tube portions 21 and 23 with respect to one another ensures that the solid substances are not carried by the exiting air stream into the exit tube 22. In the path of the vacuum stream, for example, between the air outlet opening 10 of the collecting bulb 5 and the air discharge side (pressure side) of the vacuum source 3 a screening and disinfecting filter may be provided to protect the environment.

In case a more powerful impacting and thus a deeper penetration of the crystals into the skin of the patient is desired, the flow rate of the vacuum stream may be increased by boosting the air flow (maintained by the vacuum source 3) by introducing compressed air, regulated by the flow control valve 12, into the air inlet opening 7 of the mixing bulb 4 through the pressure line 8. It is to be understood that since normal operation may be performed even without the use of compressed air from the pressure source 2, in the pressure line 8, between the air inlet opening 7 of the mixing bulb 4 and the flow control valve 12 a non-illustrated check valve may be provided to ensure air intake into the mixing bulb 4 even if the flow control valve 12 is closed.

On completion of the treatment, the handpiece 1 is moved away from the skin and the flow control valves 12, 13 are closed. The lines 8 and 11 are disconnected from the handpiece 1 which thereafter may be properly disposed of, for example, by discarding it into a sealed waste container.

Thus, the invention provides a single-use handpiece which, as a self-contained, disposable unit, incorporates both a mixing bulb containing unused abrasive crystals and a collecting bulb in which all solid matter such as used crystals and dislodged skin tissue parts are deposited, in contrast to the prior art where the hand tool as well as the bulbs which have been separate components from the hand tool are permanent, re-usable parts of the treatment apparatus, requiring stringent sterilization measures. The possibility of dispensing with such sterilization procedures translates into significant cost saving when using the invention.

It will be understood that the above description of the present invention is susceptible to various modifications, changes and adaptations, and the same are intended to be comprehended within the meaning and range of equivalents of the appended claims.

What is claimed is:

1. A manually held and guided handpiece for a skin tissue removing apparatus, said handpiece comprising
   (a) a mixing container accommodating unused abrasive crystals; said mixing container having
       (1) a front end; and
       (2) an air inlet opening spaced from said front end;
   (b) a delivery tube extending within said mixing container and having opposite first and second open ends; said first open end being situated at said front end of said mixing container and said second open end being situated at a distance from said air inlet opening;
   (c) a collecting container accommodating solid particles composed of used abrasive crystals and dislodged skin tissue fragments; said collecting container having
       (1) a front end; and
       (2) an air outlet opening spaced from said front end of said collecting container and being connectable to a vacuum source;
   (d) an exit tube extending within said collecting container and having opposite first and second open ends; said first open end of said exit tube being situated at said front end of said collecting container and said second open end of said exit tube being situated at a distance from said air outlet opening;
   (e) a connecting channel coupling said first open end of said delivery tube with said first open end of said exit tube; and
   (f) a treatment window provided in said connecting channel and being adapted to be brought into contact with a skin surface, whereby a stream of air forced to enter in said air inlet opening of said mixing container and exit said outlet opening of said collecting container entrains unused abrasive crystals from said mixing container through said delivery tube and causes the abrasive crystals to pass through said treatment window, to impinge upon the skin surface, to re-enter said treatment window with dislodged skin tissue fragments and to be deposited, together with the skin fragments, in said collecting container.

2. The handpiece as defined in claim 1, further comprising means for preventing crystals from being entrained by the air stream into said air outlet opening of said collecting container.

3. The handpiece as defined in claim 2, wherein said exit tube is a first exit tube and further wherein said means comprise
   (a) a bent terminal tube portion forming part of said first exit tube and defining said second open end thereof; and
   (b) a second exit tube having opposite first and second open ends and a bent initial tube portion defining said first open end of said second exit tube; said second open end of said first exit tube being spaced from said first open end of said second exit tube; and said second open end of said second exit tube being coupled to said air outlet opening.

4. The handpiece as defined in claim 3, wherein the bent tube portions are oriented away from one another.

5. The handpiece as defined in claim 1, wherein said treatment window is in alignment with said delivery tube.

6. The handpiece as defined in claim 1, wherein said mixing container is an elongated mixing bulb and said collecting container is an elongated collecting bulb positioned parallel to said mixing bulb; said collecting bulb and said mixing bulb together forming essentially a main body of said handpiece.

7. The handpiece as defined in claim 6, further comprising a web formed on the bulbs; further comprising a connecting tube defining said connecting channel; said connecting tube being formed on said bulbs for positioning, together with said web, said bulbs relative to one another.

8. The handpiece as defined in claim 1, further comprising a crystal intake hole provided in said delivery tube at a location spaced from said second open end thereof.

9. The handpiece as defined in claim 8, wherein said crystal intake hole is located adjacent said front end of said mixing container.

10. The handpiece as defined in claim 8, wherein said crystal intake hole has a diameter of about 1/16 inch.

* * * * *